US008071320B2

(12) United States Patent
Pronin et al.

(10) Patent No.: US 8,071,320 B2
(45) Date of Patent: Dec. 6, 2011

(54) USE OF SPECIFIC T2R TASTE RECEPTORS TO IDENTIFY COMPOUNDS THAT BLOCK BITTER TASTE

(75) Inventors: Alexey Pronin, San Diego, CA (US); Judy Connor, Vista, CA (US); Huixian Tang, San Diego, CA (US); Walter Keung, San Diego, CA (US); Guy Servant, San Diego, CA (US); Jon Elliot Adler, San Diego, CA (US); Shawn O'Connell, San Diego, CA (US); Paul Brust, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 12/854,570

(22) Filed: Aug. 11, 2010
(Under 37 CFR 1.47)

(65) Prior Publication Data

US 2010/0317035 A1    Dec. 16, 2010

Related U.S. Application Data

(60) Division of application No. 12/041,956, filed on Mar. 4, 2008, now Pat. No. 7,776,561, which is a continuation of application No. 10/191,058, filed on Jul. 10, 2002, now Pat. No. 7,338,771.

(60) Provisional application No. 60/303,811, filed on Jul. 10, 2001, provisional application No. 60/372,089, filed on Apr. 15, 2002.

(51) Int. Cl.
*G01N 33/566* (2006.01)
*C07K 14/705* (2006.01)

(52) U.S. Cl. ......... 435/7.21; 435/7.1; 435/7.2; 436/501

(58) Field of Classification Search .................. None
See application file for complete search history.

(56) References Cited

U.S. PATENT DOCUMENTS 7,244,584 B2   7/2007   Zuker et al.
7,338,771 B2   3/2008   Pronin et al.

FOREIGN PATENT DOCUMENTS

WO   01/18050    3/2001
WO   01/77676    10/2001

OTHER PUBLICATIONS

Lindemann. Receptors and transduction in taste. Nature. Sep. 13, 2001;413(6852):219-225.
Chandrashekar, et al. T2Rs function as bitter taste receptors. Cell. Mar. 17, 2000;100(6):703-711.
Wong et al. Transduction of bitter and sweet taste by gustducin. Nature. Jun. 27, 1996;381(6585):796-800.
Adler et al., A Novel Family of Mammalian Taste Receptors, Cell, Cell Press, Mar. 17, 2000, pp. 693-702, vol. 100, No. 6, Cambridge, MA, US.
Bowie et al., Deciphering the Message in Protein Sequences: Tolerance to Amino Acid Substitutions, Science, Mar. 16, 1990, pp. 1306-1310, vol. 247.
Guo et al., Protein tolerance to random amino acid change, PNAS, Jun. 22, 2004, pp. 9205-9210, vol. 10, No. 5.
Bufe et al., The human TAS2R16 receptor mediates bitter taste in response to B-glucopyranosides, Nature Genetics, Nov. 2002, pp. 397-401, vol. 32.
Conte et al., Identification and characterization of human taste receptor genes belonging to the TAS2R family, Cytogenetic and Genome Research, (2002), pp. 45-53.
Matsunami et al., A family of candidate taste receptors in human and mouse, Nature, Apr. 6, 2000, pp. 601-604, vol. 404, No. 6788.
Parry et al., Divergence of T2R chemosensory receptor families in humans, bonobos, and chimpanzees, PNAS, Oct. 12, 2004, pp. 14830-14834, vol. 101, No. 41.
Shi et al., Adaptive Diversification of Bitter Taste Receptor Genes in Mammalian Evolution, Mol. Biol. Evol., May 2003, pp. 805-814.
Smith et al., Taste processing : Whetting our appetites, Current Biology, Current Science, Jun. 17, 1999, pp. R453-R455, vol. 9, No. 12.

*Primary Examiner* — John Ulm
(74) *Attorney, Agent, or Firm* — Hunton & Williams LLP

(57) ABSTRACT

Assays for identifying compounds that modulate, preferably inhibit bitter taste associated with the activation of hT2R4, hT2R44 and/or hT2R61 are provided. The compounds identified according to these assays should modulate, e.g., inhibit bitter taste associated with bitter tasting compounds including quinine, 6-nitrosaccharin, saccharin and/or denatonium. These compounds are useful additives for foods, beverages or medicinal preparations having a bitter taste.

19 Claims, 6 Drawing Sheets

Figure 1:
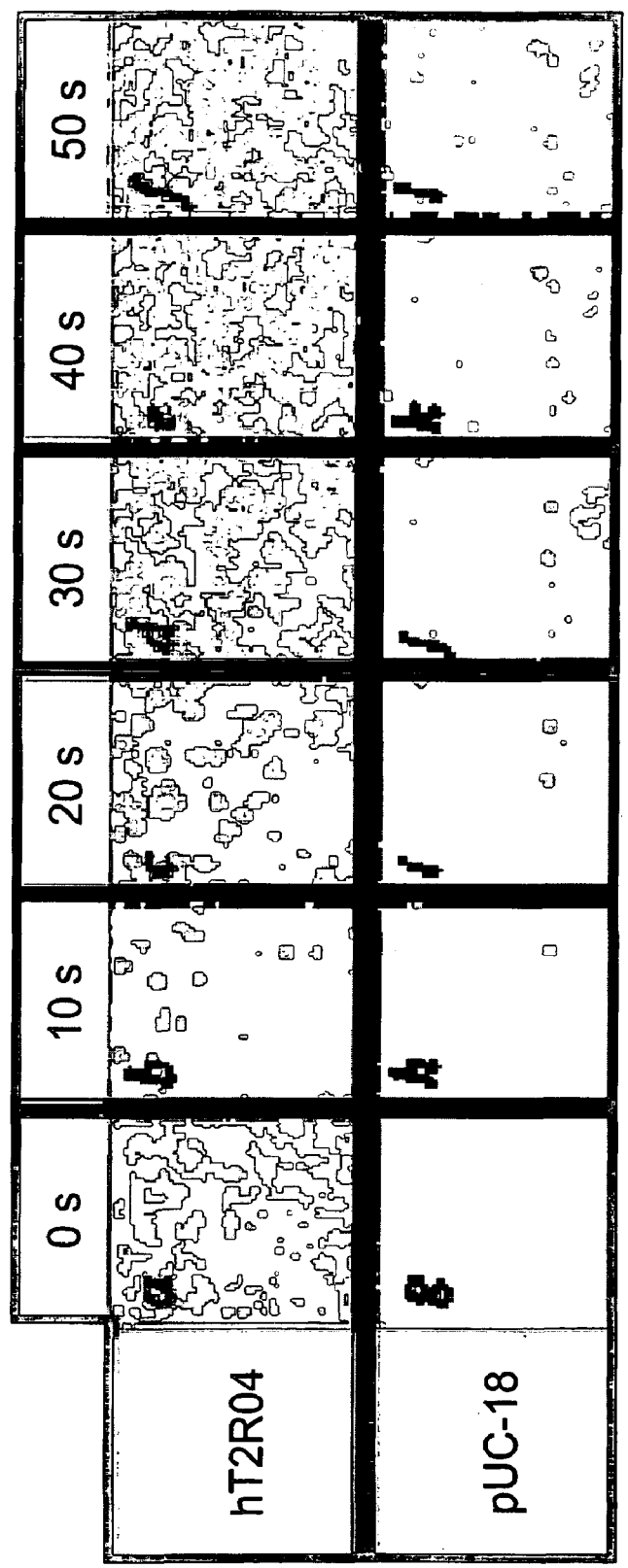

SEQUENCE LISTING

<160> NUMBER OF SEQ ID NOS: 7

<210> SEQ ID NO 1
<211> LENGTH: 300
<212> TYPE: PRT
<213> ORGANISM: Homo sapiens

<400> SEQUENCE: 1

```
Met Leu Arg Leu Phe Tyr Phe Ser Ala Ile Ile Ala Ser Val Ile Leu
 1               5                  10                  15

Asn Phe Val Gly Ile Ile Met Asn Leu Phe Ile Thr Val Val Asn Cys
                20                  25                  30

Lys Thr Trp Val Lys Ser His Arg Ile Ser Ser Asp Arg Ile Leu
            35                  40                  45

Phe Ser Leu Gly Ile Thr Arg Phe Leu Met Leu Gly Leu Phe Leu Val
            50                  55                  60

Asn Thr Ile Tyr Phe Val Ser Ser Asn Thr Glu Arg Ser Val Tyr Leu
 65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
                100                 105                 110

Phe Gln His Ser Val Phe Leu Leu Lys Arg Asn Ile Ser Pro Lys
            115                 120                 125

Ile Pro Arg Leu Leu Leu Ala Cys Val Leu Ile Ser Ala Phe Thr Thr
130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Leu Gln Phe Ile Ile Asn
                180                 185                 190

Val Thr Ser Ala Ser Leu Leu Ile His Ser Leu Arg Arg His Ile Gln
            195                 200                 205

Lys Met Gln Lys Asn Ala Thr Gly Phe Trp Asn Pro Gln Thr Glu Ala
210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
                260                 265                 270

Ser Pro Gly His Ser Val Ile Leu Ile Ile Thr His Pro Lys Leu
            275                 280                 285

Lys Thr Thr Ala Lys Lys Ile Leu Cys Phe Lys Lys
            290                 295                 300

<210> SEQ ID NO 2
<211> LENGTH: 899
<212> TYPE: DNA
<213> ORGANISM: Homo sapiens

<400> SEQUENCE: 2
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240
tctgcttttt ttgtgttgtg tttcatgttt ttggactcga gcagtgtctg gtttgtgacc     300
ttgctcaata tcttgtactg tgtgaagatt actaacttcc aacactcagt gtttctcctg     360
ctgaagcgga atatctcccc aaagatcccc aggctgctgc tggcctgtgt gctgatttct     420
gctttcacca cttgcctgta catcacgctt agccaggcat cacctttccc tgaacttgtg     480
```

-continued

```
actacgagaa ataacacatc atttaatatc agtgagggca tcttgtcttt agtggtttct    540
ttggtcttga gctcatctct ccagttcatc attaatgtga cttctgcttc cttgctaata    600
cactccttga ggagacatat acagaagatg cagaaaaatg ccactggttt ctggaatccc    660
cagacggaag ctcatgtagg tgctatgaag ctgatggtct atttcctcat cctctacatt    720
ccatattcag ttgctaccct ggtccagtat ctccccdttt atgcagggat ggatatgggg    780
accaaatcca tttgttctga ttttgccacc ctttactctc caggcattct gttctcatta    840
ttatcacaca tcctaaactg aaaacaacag caaagaagat tctttgtttc aaaaaatag    899
```

<210> SEQ ID NO 3
<211> LENGTH: 319
<212> TYPE: PRT
<213> ORGANISM: Homo sapiens

<400> SEQUENCE: 3

```
Met Ile Thr Phe Leu Pro Ile Ile Phe Ser Ile Leu Ile Val Val Ile
  1               5                  10                  15

Phe Val Ile Gly Asn Phe Ala Asn Gly Phe Ile Ala Leu Val Asn Ser
             20                  25                  30

Ile Glu Trp Val Lys Arg Gln Lys Ile Ser Phe Val Asp Gln Ile Leu
         35                  40                  45

Thr Ala Leu Ala Val Ser Arg Val Gly Leu Leu Trp Val Leu Leu Leu
     50                  55                  60

His Trp Tyr Ala Thr Gln Leu Asn Pro Ala Phe Tyr Ser Val Glu Val
 65                  70                  75                  80

Arg Ile Thr Ala Tyr Asn Val Trp Ala Val Thr Asn His Phe Ser Ser
                 85                  90                  95

Trp Leu Ala Thr Ser Leu Ser Met Phe Tyr Leu Leu Arg Ile Ala Asn
            100                 105                 110

Phe Ser Asn Leu Ile Phe Leu Arg Ile Lys Arg Val Lys Ser Val
            115                 120                 125

Val Leu Val Ile Leu Leu Gly Pro Leu Leu Phe Leu Val Cys His Leu
        130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300
```

Ser Leu Arg Leu His Arg Phe Thr Arg Gly Ala Leu Cys Val Phe
305                 310                 315

<210> SEQ ID NO 4
<211> LENGTH: 960
<212> TYPE: DNA
<213> ORGANISM: Homo sapiens

<400> SEQUENCE: 4

```
atgataactt ttctgcccat catttttttcc attctaatag tggttatatt tgtgattgga    60
aattttgcta atggcttcat agcattggta aattccattg agtgggtcaa gagacaaaag   120
atctccttg ttgaccaaat tctcactgct ctggcggtct ccagagttgg tttgctctgg   180
gtgttattac tacattggta tgcaactcag ttgaatccag cttttttatag tgtagaagta   240
agaattactg cttataatgt ctgggcagta accaaccatt tcagcagctg gcttgctact   300
agcctcagca tgttttattt gctcaggatt gccaatttct ccaaccttat ttttcttcgc   360
ataaagagga gagttaagag tgttgttctg gtgatactgt gggggccttt gctatttttg   420
gtttgtcatc ttttttgtgat aaacatggat gagactgtat ggacaaaaga atatgaagga   480
aacgtgactt ggaagatcaa attgaggagt gcaatgtacc attcaaatat gactctaacc   540
atgctagcaa actttgtacc cctcactctg accctgatat cttttctgct gttaatctgt   600
tctctgtgta acatctcaa gaagatgcag ctccatggca aaggatctca agatcccagc   660
accaaggtcc acataaaagc tttgcaaact gtgacctcct tcttctgtt atgtgccatt   720
tactttctgt ccatgatcat atcagtttgt aatttgggga ggctggaaaa gcaacctgtc   780
ttcatgttct gccaagctat tatattcagc tatccttcaa cccacccatt catcctgatt   840
tgggaaaaca gaagctaaa gcagatttt ctttcagttt tgcggcatgt gaggtactgg   900
gtgaaagaca gaagccttcg tctccataga ttcacaagag gggcattgtg tgtcttctag   960
```

<210> SEQ ID NO 5
<211> LENGTH: 309
<212> TYPE: PRT
<213> ORGANISM: Homo sapiens

<400> SEQUENCE: 5

Met Ile Thr Phe Leu Pro Ile Ile Phe Ser Ser Leu Val Val Thr
1               5                   10                  15

Phe Val Ile Gly Asn Phe Ala Asn Gly Phe Ile Ala Leu Val Asn Ser
                20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
                100                 105                 110

Phe Ser Asn Phe Ile Phe Leu His Leu Lys Arg Arg Val Lys Ser Val
            115                 120                 125

Ile Leu Val Met Leu Leu Gly Pro Leu Leu Phe Leu Ala Cys His Leu
        130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
            165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
            195                 200                 205

Met Gln Leu His Gly Lys Gly Ser Gln Asp Pro Ser Thr Lys Val His
210                 215                 220

Ile Lys Ala Leu Gln Thr Val Ile Ser Phe Leu Leu Cys Ala Ile
225                 230                 235                 240

Tyr Phe Leu Ser Ile Met Ile Ser Val Trp Ser Phe Gly Ser Leu Glu
            245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
            275                 280                 285

Thr Phe Leu Ser Val Phe Trp Gln Met Arg Tyr Trp Val Lys Gly Glu
            290                 295                 300

Lys Thr Ser Ser Pro
305

<210> SEQ ID NO 6
<211> LENGTH: 930
<212> TYPE: DNA
<213> ORGANISM: Homo sapiens

<400> SEQUENCE: 6
atgataactt ttctacccat cattttttcc agtctggtag tggttacatt tgttattgga      60
aattttgcta atggcttcat agcactggta aattccattg agtggttcaa gagacaaaag     120
atctccttttg ctgaccaaat tctcactgct ctggcggtct ccagagttgg tttgctctgg    180
gtattattat taaactggta ttcaactgtg ttgaatccag cttttaatag tgtagaagta     240
agaactactg cttataatat ctgggcagtg atcaaccatt tcagcaactg gcttgctact     300
accctcagca tattttattt gctcaagatt gccaatttct ccaactttat ttttcttcac     360
ttaaagagga gagttaagag tgtcattctg gtgatgttgt tggggccttt gctattttg      420
gcttgtcatc ttttttgtgat aaacatgaat gagattgtgc ggacaaaaga atttgaagga    480
aacatgactt ggaagatcaa attgaagagt gcaatgtact tttcaaatat gactgtaacc    540
atggtagcaa acttagtacc cttcactctg accctactat cttttatgct gttaatctgt    600
tctttgtgta acatctcaa gaagatgcag ctccatggta aaggatctca agatcccagc     660
accaaggtcc acataaaagc tttgcaaact gtgatctcct cctcttgtt atgtgccatt    720
tactttctgt ccataatgat atcagttttgg agttttggaa gtctggaaaa caaacctgtc    780
ttcatgttct gcaaagctat tagattcagc tatccttcaa tccacccatt catcctgatt    840
tggggaaaca agaagctaaa gcagactttt ctttcagttt tttggcaaat gaggtactgg    900
gtgaaaggag agaagacttc atctccatag                                    930

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:
       Illustrative translocation domain

```
-continued

<400> SEQUENCE: 7

Met Asn Gly Thr Glu Gly Pro Asn Phe Tyr Val Pro Phe Ser Asn Lys
 1               5                  10                  15

Thr Gly Val Val
            20
```

USE OF SPECIFIC T2R TASTE RECEPTORS TO IDENTIFY COMPOUNDS THAT BLOCK BITTER TASTE

RELATED APPLICATIONS

This application is a divisional of U.S. application Ser. No. 12/041,956 filed Mar. 4, 2008, which is a continuation of Ser. No. 10/191,058 filed Jul. 10, 2002 (U.S. Pat. No. 7,338,771), which claims priority to provisional application U.S. Ser. No. 60/303,811 filed on Jul. 10, 2001 and provisional application U.S. Ser. No. 60/372,089, filed on Apr. 15, 2002 which are incorporated by reference in their entirety herein.

FIELD OF THE INVENTION

The present invention involves the elucidation of bitter compounds that activate several previously reported human G-protein coupled receptors (GPCRs) that are involved in taste perception. Particularly the invention involves the discovery that specific taste receptors in the T2R family are specifically activated by bitter compounds, i.e., that the human T2R4 taste receptor is specifically activated by the bitter alkaloid quinine, that the human T2R61 taste receptor is specifically activated by a bitter derivative of saccharin, 6-nitrosaccharin and that the human T2R44 receptor is specifically activated by denatonium and to a lesser extent by 6-nitrosaccharin. Based on these discoveries, these human taste receptors, fragments, or variants or chimeras thereof, including orthologs, splice variants, single nucleotide polymorphisms (SNPS), and genetically engineered mutants thereof, are useful in assays, preferably high throughput cell-based assays for identifying compounds that block the bitter taste of quinine, 6-nitrosaccharin and denatonium, as well as structurally related compounds and other compounds that activate these receptors. Compounds identified using these assays may be used as ingredients in foods, beverages or medicinal products to improve the taste thereof.

DESCRIPTION OF THE RELATED ART

One of the basic taste modalities that humans can recognize is bitter. The physiology of bitter taste until quite recently was very poorly understood. Recent studies have started to shed light on the biology of taste (Lindemann, Nature (2001)). It is now believed that many bitter compounds produce bitter taste by interacting with cell surface receptors. These receptors belong to the family of seven transmembrane domain receptors that interact with intracellular G proteins. A novel family of GPCRs, termed T2Rs, has been identified in humans and rodents (Adler et al., Cell 100(6):693-702 (2000); Chandrashekar et al., Cell 100(6): 703-711 (2000); Matsunami H, Montmayeur J P, Buck L B. Nature 404(6778): 601-4 (2000)). Several lines of evidence suggest that T2Rs mediate responses to bitter compounds. First, T2R genes are specifically expressed in subset of taste receptor cells of the tongue and palate epithelia. Second, the gene for one of the human T2Rs (hT2R1) is located in a chromosomal locus that is linked to sensitivity to bitter compound 6-n-propyl-2-thiouracil in humans (Adler et al., (Id.) (2000)). Third, one of the mouse T2Rs (mT2R5) is located in a chromosomal locus that is linked to sensitivity to bitter compound cycloheximide in mice. It was also shown that mT2R5 can activate gustducin, G protein specifically expressed in taste cells and linked to bitter stimuli transduction (Wong et al., Nature 381:796-800 (1996)). Gustducin activation by mT2R5 occurs only in response to cycloheximide (Chandrashekar et al., (Id.) (2000). Thus, it has been proposed that mT2R family mediates bitter taste response in mice, whereas hT2R family mediates bitter taste response in humans. Only one human T2R was suggested as having identified bitter ligand—hT2R4 was shown as being activated by denatonium (Chandrashekar et al., (Id.) 2000). However, effective denatonium concentrations used in the study (1.5 mM) were unusually high, i.e., is $10^5$-fold higher than the reported bitter threshold for denatonium to humans (Saroli, Naturwissenschaften 71:428-429 (1984)). Thus, no specific bitter ligand was convincingly matched to any hT2R. It has been also suggested that each hT2R is able to bind multiple bitter ligands. This hypothesis is based on the fact that hT2R family consists of only 24 identified members, whereas humans can recognize hundreds of different compounds as bitter. Sequences of hT2Rs have been previously reported and are discloses in published PCT applications by Zuker et al. (WO 01/18050 A2, (2001)) and Adler et al. (WO 01/77676 A1 (2001)) both of which are incorporated by reference in their entirety herein.

One of the difficulties of studying T2R function is that these receptors are not readily expressed in cultured mammalian cell lines. To improve T2R expression an N-terminal sequence from well-expressed GPCR, rhodopsin, was attached to T2R sequences (Chandrashekar et al., (Id.) 2000). This N-terminal tag also allowed easy monitoring of protein expression due to available antibody. Whereas the incorporation of the rhodopsin tag improved expression of some T2Rs in mammalian cell lines, many of them still were not expressed well enough for functional studies. In a different approach mT2R5 was successfully expressed in insect Sf9 cells and used for functional studies using biochemical GTPγS binding assay (Chandrashekar et al., (Id.) 2000).

However, notwithstanding what has been reported there still is a lack of uncertainty as to the function of the T2R gene family. Particularly, there is a lack of understanding as to what taste compounds activate particular T2R receptors. A greater understanding of the binding properties of different T2Rs would be highly beneficial as it will greater facilitate the use thereof in selecting compounds having desired taste modulatory properties.

SUMMARY OF THE INVENTION

Toward that end, the parent invention relates to the discovery that several taste receptors in the T2R family, particularly hT2R4, hT2R61 and hT2R44 are respectively specifically activated by the bitter compounds, quinine; 6-nitrosaccharin; and denatonium (and to a lesser extent by 6-nitrosaccharin).

These discoveries were made using cell-based assays that measured the activity of T2Rs using cells that express a particular T2R. In particular, as described in greater detail infra, HEK-Gα$_{15}$ cell lines expressing hT2R4 on their surface were used in cell-based assays that detected changes in intracellular calcium concentrations, and were found to be specifically activated by quinine whereas other hT2Rs were not activated under similar conditions. It was also shown that quinine activates hT2R4 in a typical dose-response relationship.

Additionally, as described in greater detail infra, a GTPγS binding assay was used to monitor the activity of human T2Rs expressed in insect cells (Sf9 cells) using a baculovirus expression system, in the presence of various bitter compounds. The results of this assay indicate that hT2R61 is specifically activated by 6-nitrosaccharin and that hT2R44 is specifically activated by denatonium (and to a lesser extent by 6-nitrosaccharin).

Therefore, the invention embraces the use of hT2R4, hT2R44 and hT2R61 in assays, preferably high-throughput assays, to identify compounds that block the activation of these receptors by quinine, 6-nitrosaccharin, denatonium or related compounds such as saccharin.

The invention also embraces methods which include confirmation that these compounds block bitter taste in taste tests. Also, the invention embraces the use of the identified compounds in foods, beverages and medicines in order to inhibit bitter taste, e.g., saccharin containing diet beverages, foods or medicinal products.

OBJECTS OF THE INVENTION

It is an object of the invention to identify compounds that block the activation of hT2R4 or fragments, variants, orthologs, or chimeras thereof by quinine or a compound structurally related to quinine that activates hT2R4.

It is another object of the invention to identify compounds that block the activation of hT2R61 or fragments, variants, orthologs, or chimera thereof by 6-nitrosaccharin, saccharin or a compound structurally related thereto that activates hT2R61.

It is another object of the invention to identify compounds that block the activation of hT2R44 by denatonium or 6-nitrosaccharin or a compound structurally related thereto that specifically activates hT2R44.

It is a more specific object of the invention to use cells that stably or transiently express hT2R4, hT2R61 or hT2R44, or a fragment, variant, ortholog or chimera thereof, in cell-based assays to identify compounds that block the activation of the above-identified T2R receptors respectively by quinine; 6-nitrosaccharin or saccharin; or denatonium or 6-nitrosaccharin, as a means of identifying compounds that block bitter taste elicited by these receptors.

It is an even more specific object of the invention to use mammalian or insect cells, e.g., HEK-293T cells that express G15 protein in cell based assays that detect changes in intracellular calcium, preferably using calcium-specific fluorescent dyes, to identify compounds that block the activation of hT2R4 by quinine or related compounds, hT2R61, by 6-nitrosaccharin, saccharin or related compounds, or hT2R44 by denatonium or related compounds as a means for identifying compounds that block the specific activation of these T2Rs, particularly by bitter tasting compounds.

It is another specific object of the invention to use mammalian or insect cells, e.g. Sf9 cells, that express hT2R4, hT2R44 or hT2R61, in GTPγS binding assays to identify compounds that respectively block the activation of these receptors by quinine, denatonium, 6-nitrosaccharin or saccharin as a means of identifying compounds that block the specific activation of these T2Rs, particularly by bitter tasting compounds.

It is another object of the invention to confirm that the identified compounds block bitter taste, e.g. that elicited by quinine, denatonium, 6-nitrosaccharin or saccharin in taste tests.

It is another object of the invention to utilize compounds identified in the assays described herein as additives in compositions to block bitter taste induced by compounds that specifically activate hT2R4, hT2R44 or hT2R61. A preferred object of the invention is to use a compound that inhibits activation of hT2R61 and/or hT2R44 by 6-nitrosaccharin or saccharin to block the bitter taste of saccharin containing compositions, particularly diet beverages.

DETAILED DESCRIPTION OF THE FIGURES

FIG. 1 contains the results of a cell-based assay using HEK-G15 cells that express hT2R4, the results of which show that quinine elicits calcium mobilization by hT2R4. In this assay, HEK-G15 cells were transfected with hT2R4 or a carrier DNA (pUC-18) and two days later assayed using single cell calcium imaging. Panels a to f correspond to responses of cells expressing hT2R4 after 0, 10, 20, 30, 40 and 50 seconds of stimulation with quinine (250 µM final). Panels g to l correspond to responses of cells expressing puc-18 after 0, 10, 20, 30, 40 and 50 seconds of stimulation with quinine (250 µM final).

Figure 2:
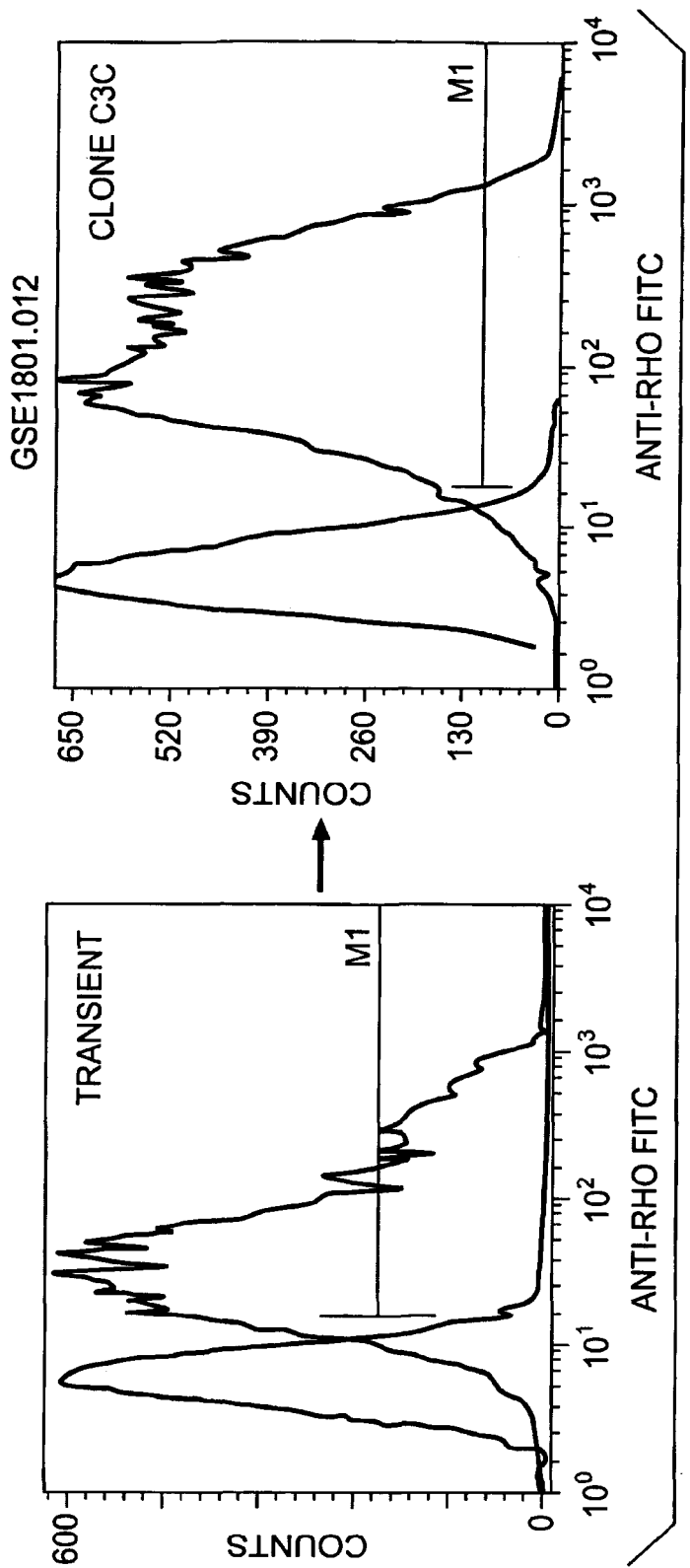

FIG. 2 contains the results of an experiment that used a stable HEK-G15 cell line expressing hT2R4 on its surface. In this experiment a clone of HEK-G15 expressing high levels of hT2R4 on its cell surface was obtained after two rounds of sort using FACS and cloning from the twice-sorted population. FACS analysis revealed that the sorted clones express roughly 2-3 times more T2R receptor on their cell surface than transiently transfected cells.

Figure 3:
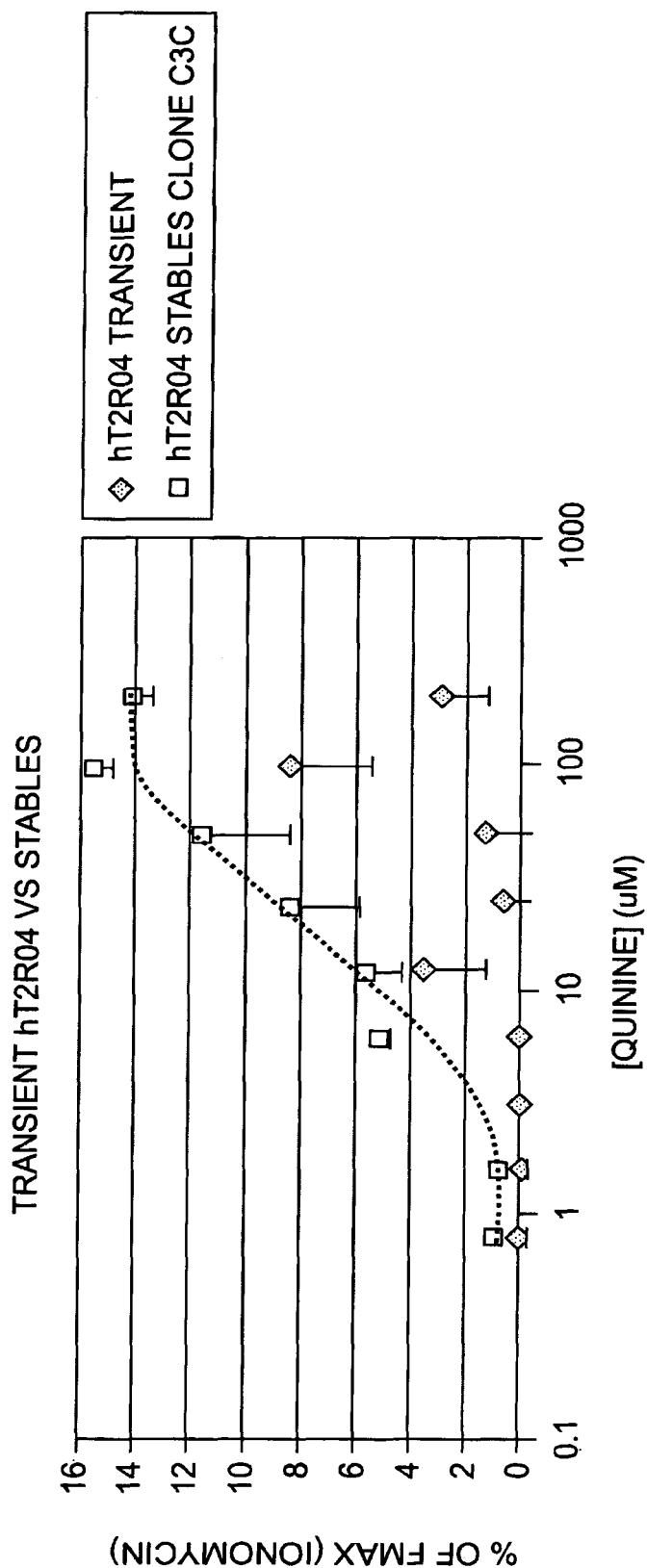

FIG. 3 shows the dose-response relationship of quinine on hT2R4 induced calcium mobilization on a clone of HEK-G15 stably expressing hT2R4 (clone C3C) plated onto 96 well plates. For comparison purposes, cells transiently transfected with hT2R4 were plated onto another set of plates. The effect of increasing doses of quinine was tested using FLIPR. These results show a clear dose-response relationship in the clone that stably expresses high levels of hT2R4.

Figure 4:
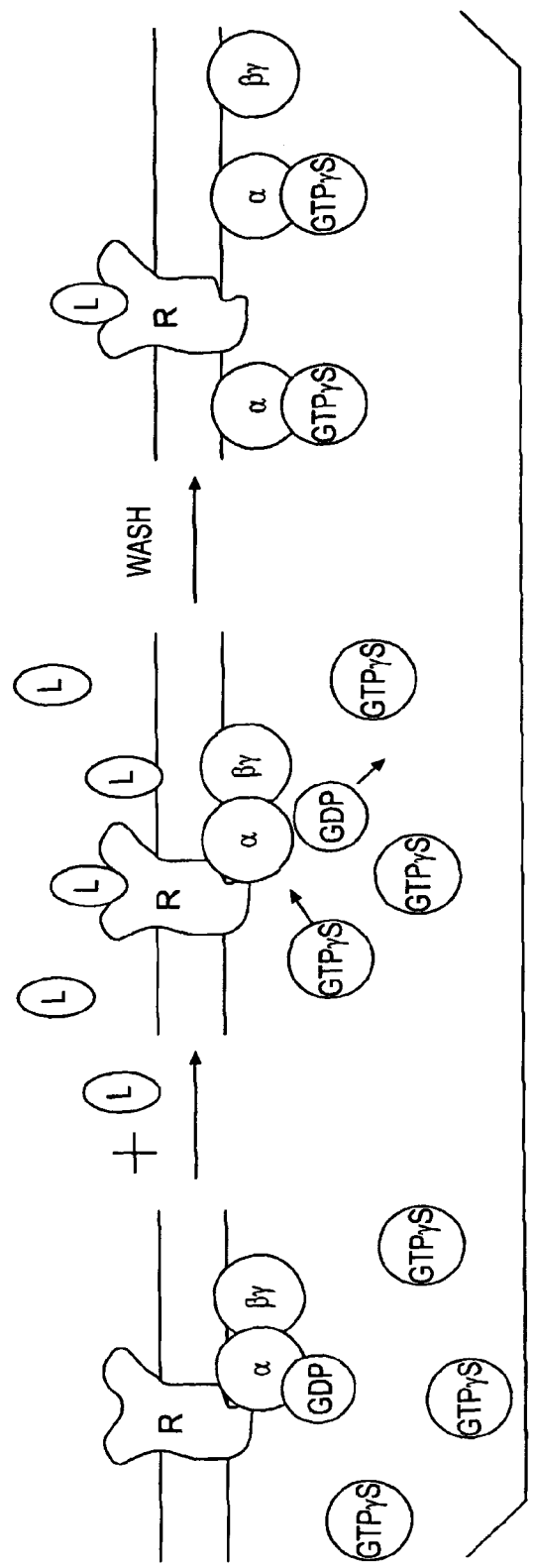

FIG. 4 is a schematic diagram of the GTPγS binding assay used to identify compounds that activate hT2Rs. In the schematic, "R" is hT2R, αβγ is G protein, and "L" is a ligand that activates the receptor.

Figure 5:
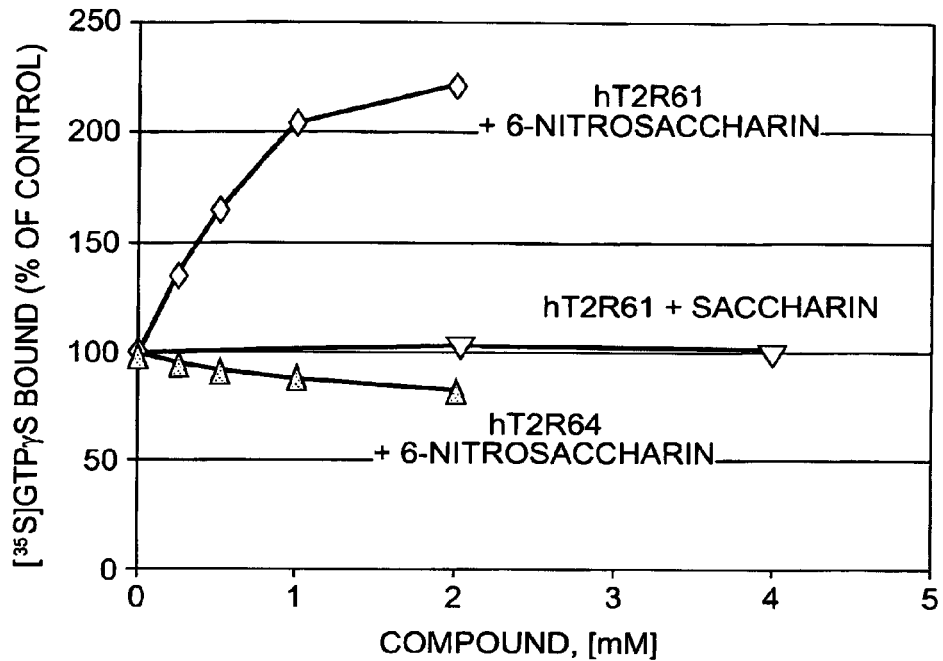

FIG. 5 contains the results of a GTPγS binding assay that shows that 6-nitrosaccharin activates hT2R61 but not hT2R64 under the same conditions. The activity of hT2R61 and hT2R64 was determined using a GTPγS binding assay in the absence or presence of the indicated concentrations of 6-nitrosaccharin or saccharin (wherein activity is expressed as the percentage of activity in the absence of added test compounds).

Figure 6:
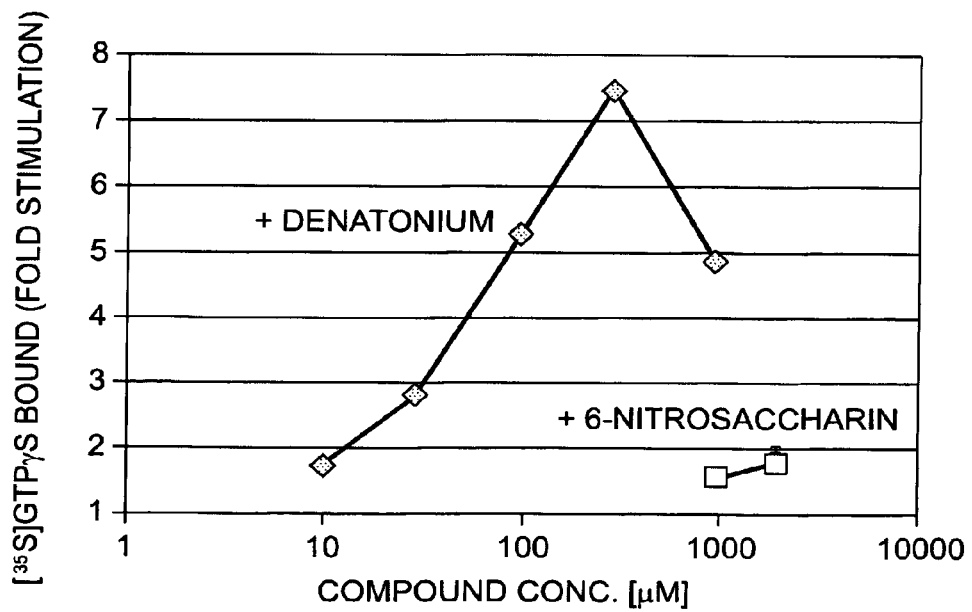

FIG. 6 contains the results of a GTPγS binding assay which indicates that hT2R44 is activated by denatonium and 6-nitrosaccharin. The activity is expressed as the fold-stimulation relative to the activity in the absence of added test compounds.

Figure 7:
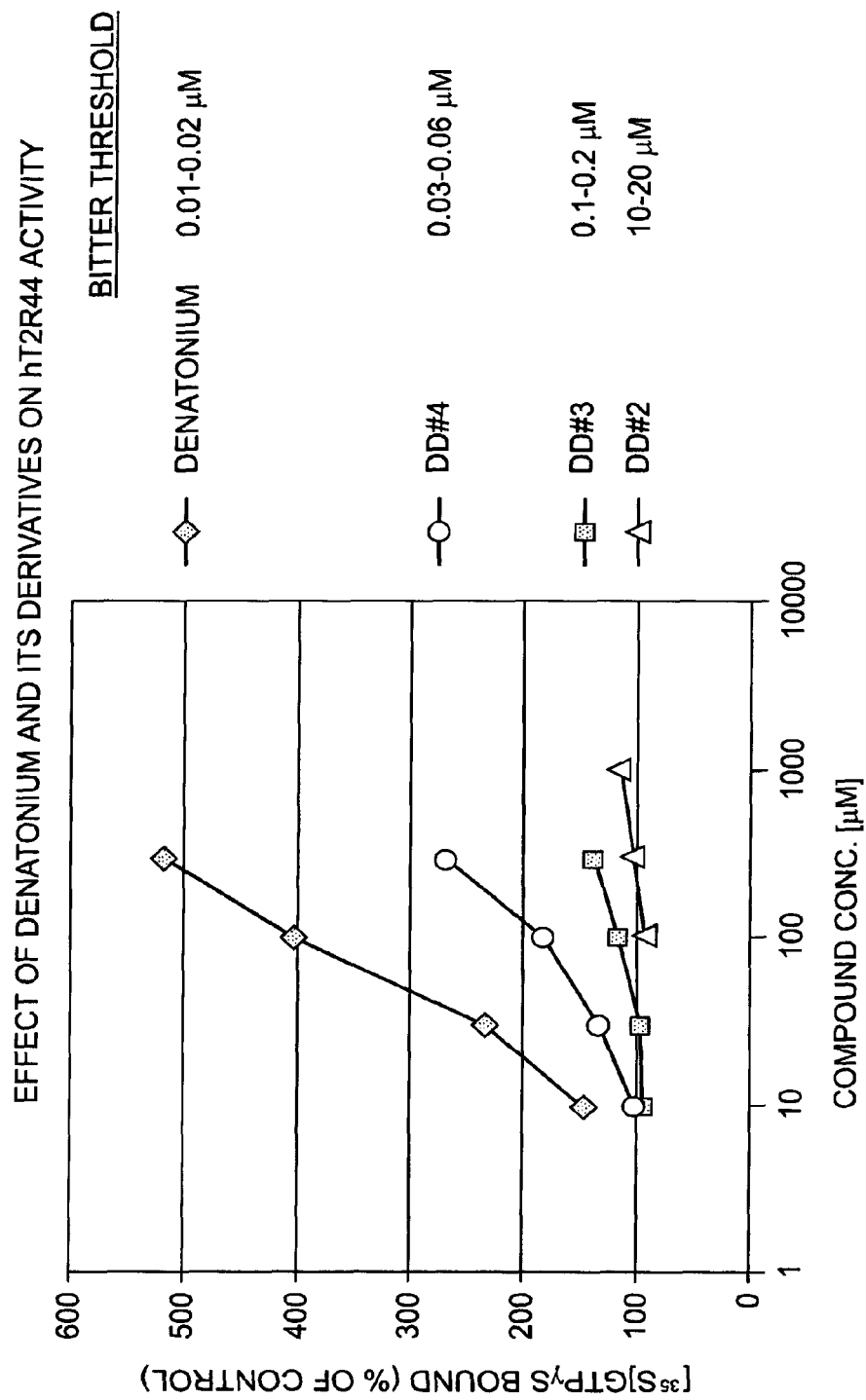

FIG. 7 contains the results of a GTPγS binding assay evaluating the effects of denatonium and derivatives thereof on hT2R44 activity. (In the figure bitter thresholds are obtained from A. Saroli (Id.) (1984) and A. Saroli Z. Lebensen Unters Forsch 180:227-221 (1985)).

DETAILED DESCRIPTION OF THE INVENTION

Prior to specifically describing the invention, the following definitions are provided.

The term "T2R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T2Rs disclosed infra, and in the Zuker (Id) (2001) and Adler (Id.) (2001) applications incorporated by reference over a window of about 25 amino acids, optimally 50-100 amino acids; (2) specifically bind to antibodies raised against an immunogen comprising an amino acid sequence selected from the group consisting of the T2R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T2R DNA sequences disclosed infra, and conservatively modified variants thereof; (4) comprise a sequence at least about 40% identical to an amino acid sequence selected from the group consisting of the T2R amino acid sequences disclosed infra or (5) are amplified by primers that specifically hybridize under stringent hybridization conditions to the described T2R sequences.

As previously discussed, while T2R genes exhibit substantial sequence divergence at both the protein and DNA level, all T2Rs isolated to date have been found to contain certain consensus sequences in particular regions that are identical or which possess or at least 70-75% sequence identity to the T2R consensus sequence identified previously in the Adler et al (WO 01/77676 A1 (2001) and Zuker et al. WO 01/18050 A2, both incorporated by reference in their entirety herein.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al., *Cell*, 96:541-51 (1999); Buck & Axel, *Cell*, 65:175-87 (1991)). These regions can be structurally identified using methods known to those of skill in the art, such as sequence analysis programs that identify hydrophobic and hydrophilic domains (see, e.g., Stryer, *Biochemistry*, (3rd ed. 1988); see also any of a number of Internet based sequence analysis programs, such as those found at dot.imgen.bcm.t-mc.edu). These regions are useful for making chimeric proteins and for in vitro assays of the invention, e.g., ligand binding assays.

A "T2R4" according to the claimed invention is intended to include human T2R4 polypeptides and the corresponding nucleic acid sequences, as well as fragments, variants, mutants and orthologs thereof that possess similar function, i.e., which are specifically activated by quinine or other bitter compounds. The sequences for human T2R4 are contained in Zuker et al. (WO 01/18050) A2 (2001) and Adler et al. (WO 01/77676 A1 (2001)) are contained in SEQ ID NOS: 1 and 2 (human T2R4 protein and DNA) set forth below.

SEQ ID NO: 1
Human T2R4 amino acid sequence
MLRLFYFSAIIASVILNFVGIIMNLFITVVNCKTWVKSHRISSSDRIL
FSLGITRFLMLGLFLVNTIYFVSSNTERSVYLSAFFVLCFMFLDSSSV
WFVTLLNILYCVKITNFQHSVFLLLKRNISPKIPRLLLACVLISAFTT
CLYITLSQASPFPELVTTRNNTSFNISEGILSLVVSLVLSSSLQFIIN
VTSASLLIHSLRRHIQKMQKNATGFWNPQTEAHVGAMKLMVYFLILYI
PYSVATLVQYLPFYAGMDMGTKSICLIFATLYSPGHSVILIIITHPKL
KTTAKKILCFKK SEQ ID NO: 2
Human T2R4 nucleotide sequence
ATGCTTCGGTTATTCTATTTCTCTGCTATTATTGCCTCAGTTATTTTA
AATTTTGTAGGAATCATTATGAATCTGTTTATTACAGTGGTCAATTGC
AAAACTTGGGTCAAAAGCCATAGAATCTCCTCTTCTGATAGGATTCTG
TTCAGCCTGGGCATCACCAGGTTTCTTATGCTGGACTATTTCTGGTG
AACACCATCTACTTCGTCTCTTCAAATACGGAAAGGTCAGTCTACCTG
TCTGCTTTTTTGTGTTGGTTTCATGTTTTTGGACTCGAGCAGTGTC
TGGTTTGTGACCTTGCTCAATATCTTGTACTGTGTGAAGATTACTAAC
TTCCAACACTCAGTGTTTCTCCTGCTGAAGCGGAATATCTCCCCAAAG
ATCCCCAGGCTGCTGCTGGCCTGTGTGCTGATTTCTGCTTTCACCACT
TGCCTGTACATCACGCTTAGCCAGGCATCACCTTTTCCTGAACTTGTA
ACTACGAGAAATAACACATCATTTAATATCAGTGAGGGCATCTTGTCT
TTAGTGGTTTCTTTGGTCTTGAGCTCATCTCTCCAGTTCATCATTAAT
GTGACTTCTGCTTCCTTGCTAATACACTCCTTGAGGAGACATATACAG
AAGATGCAGAAAAATGCCACTGGTTTCTGGAATCCCCAGACGGAAGCT
CATGTAGGTGCTATGAAGCTGATGGTCTATTTCCTCATCCTCTACATT
CCATATTCAGTTGCTACCCTGGTCCAGTATCTCCCCTTTTATGCAGGG
ATGGATATGGGGACCAAATCCATTTGTTCTGATTTTGCCACCCTTTAC
TCTCCAGGCATTCTGTTCTCATTATTATCACACATCCTAAACTGAAAA
CAACAGCAAAGAAGATTCTTTGTTTCAAAAAATAG

A "T2R44" according to the invention is intended to include human T2R44 having the protein and DNA sequences contained in SEQ ID NOS: 3 and 4 below, and fragments, chimeras, variants, mutants, orthologs, including e.g., splice variants, allelic variants, and single nucleotide polymorphisms, that exhibit similar function, i.e., which are specifically activated by bitter compounds such as denatonium as determined by appropriate assays.

SEQ ID NO.: 3
Human T2R44 amino acid sequence
>hT2R44 (Zuker 2001)
MITFLPIIFSILIVVIFVIGNFANGFIALVNSIEWVKRQKISFVDQIL
TALAVSRVGLLWVLLLHWYATQLNPAFYSVEVRITAYNVWAVTNHFSS
WLATSLSMFYLLRIANFSNLIFLRIKRRVKSVVLVILLGPLLFLVCHL
FVINMDETVWTKEYEGNVTWKIKLRSAMYHSNMTLTMLANFVPLTLTL
ISFLLLICSLCKHLKKMQLHGKGSQDPSTKVHIKALQTVTSFLLLCAI
YFLSMIISVCNLGRLEKQPVFMFCQAIIFSYPSTHPFILILGNKKLKQ
IFLSVLRHVRYWVKDRSLRLHRFTRGALCVF SEQ ID NO.: 4
Human T2R44 nucleotide sequence
ATGATAACTTTTCTGCCCATCATTTTTTCCATTCTAATAGTGGTTATA
TTTGTGATTGGAAATTTTGCTAATGGCTTCATAGCATTGGTAAATTCC
ATTGAGTGGGTCAAGAGACAAAAGATCTCCTTTGTTGACCAAATTCTC
ACTGCTCTGGCGGTCTCCAGAGTTGGTTTGCTCTGGGTGTTATTACTA
CATTGGTATGCAACTCAGTTGAATCCAGCTTTTTATAGTGTAGAAGTA
AGAATTACTGCTTATAATGTCTGGGCAGTAACCAACCATTTCAGCAGC
TGGCTTGCTACTAGCCTCAGCATGTTTTATTTGCTCAGGATTGCCAAT
TTCTCCAACCTTATTTTTCTTCGCATAAAGAGGAGAGTTAAGAGTGTT
GTTCTGGTGATACTGTTGGGGCCTTTGCTATTTTTGGTTTGTCATCTT
TTTGTGATAAACATGGATGAGACTGTATGGACAAAAGAATATGAAGGA
AACGTGACTTGGAAGATCAAATTGAGGAGTGCAATGTACCATTCAAAT
ATGACTCTAACCATGCTAGCAAACTTTGTACCCCTCACTCTGACCCTG
ATATCTTTTCTGCTGTTAATCTGTTCTCTGTGTAAACATCTCAAGAAG
ATGCAGCTCCATGGCAAAGGATCTCAAGATCCCAGCACCAAGGTCCAC
ATAAAAGCTTTGCAAACTGTGACCTCCTTTCTTCTGTTATGTGCCATT
TACTTTCTGTCCATGATCATATCAGTTTGTAATTTGGGGAGGCTGGAA
AAGCAACCTGTCTTCATGTTCTGCCAAGCTATTATATTCAGCTATCCT
TCAACCCACCCATTCATCCTGATTTTGGGAAACAAGAAGCTAAAGCAG
ATTTTTCTTTCAGTTTTGCGGCATGTGAGGTACTGGGTGAAAGACAGA
AGCCTTCGTCTCCATAGATTCACAAGAGGGGCATTGTGTGTCTTCTAG A "T2R61" according to the invention is intended to include the human T2R61 protein contained in SEQ ID NO: 5 and the corresponding nucleic acid sequence (SEQ ID NO: 6) and fragments, chimeras, variants, mutants including allelic, splice and single nucleotide polymorphisms, and orthologs that possess similar function, i.e., which are specifically activated by 6-nitrosaccharin, saccharin, or related bitter compounds as determined screened using appropriate assays.

SEQ ID NO.: 5
Human T2R61 amino acid sequence
>hT2R61 (Adler 2001)
MITFLPIIFSSLVVVTFVIGNFANGFIALVNSIEWFKRQKISFADQIL
TALAVSRVGLLWVLLLNWYSTVLNPAFNSVEVRTTAYNIWAVINHFSN
WLATTLSIFYLLKIANFSNFIFLHLKRRVKSVILVMLLGPLLFLACHL
FVINMNEIVRTKEFEGNMTWKIKLKSAMYFSNMTVTMVANLVPFTLTL
LSFMLLICSLCKHLKKMQLHGKGSQDPSTKVHIKALQTVISFLLLCAI
YFLSIMISVWSFGSLENKPVFMFCKAIRFSYPSIHPFILIWGNKKLKQ
TFLSVFWQMRYWVKGEKTSSP SEQ ID NO.: 6
Human T2R61 nucleotide sequence for hT2R61
ATGATAACTTTTCTACCCATCATTTTTTCCAGTCTGGTAGTGGTTACA
TTTGTTATTGGAAATTTTGCTAATGGCTTCATAGCACTGGTAAATTCC
ATTGAGTGGTTCAAGAGACAAAAGATCTCCTTTGCTGACCAAATTCTC
ACTGCTCTGGCGGTCTCCAGAGTTGGTTTGCTCTGGGTATTATTATTA
AACTGGTATTCAACTGTGTTGAATCCAGCTTTTAATAGTGTAGAAGTA
AGAACTACTGCTTATAATATCTGGGCAGTGATCAACCATTTCAGCAAC
TGGCTTGCTACTACCCTCAGCATATTTTATTTGCTCAAGATTGCCAAT
TTCTCCAACTTTATTTTTCTTCACTTAAAGAGGAGAGTTAAGAGTGTC
ATTCTGGTGATGTTGTTGGGGCCTTTGCTATTTTTGGCTTGTCATCTT

```
                    -continued
TTTGTGATAAACATGAATGAGATTGTGCGGACAAAAGAATTTGAAGGA
AACATGACTTGGAAGATCAAATTGAAGAGTGCAATGTACTTTTCAAAT
ATGACTGTAACCATGGTAGCAAACTTAGTACCCTTCACTCTGACCCTA
CTATCTTTTATGCTGTTAATCTGTTCTTTGTGTAAACATCTCAAGAAG
ATGCAGCTCCATGGTAAAGGATCTCAAGATCCCAGCACCAAGGTCCAC
ATAAAAGCTTTGCAAACTGTGATCTCCTTCCTCTTGTTATGTGCCATT
TACTTTCTGTCCATAATGATATCAGTTTGGAGTTTTGGAAGTCTGGAA
AACAAACCTGTCTTCATGTTCtgcaaagctattagattcagctatcct
tcaatccacccattcatcctgatttggggaaacaagaagctaaagcag
acttttctttcagtttttggcaaatgaggtactgggtgaaaggagag
aagacttcatctccatag
```

"Extracellular domains" therefore refers to the domains of T2R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, *J. Mol. Biol.*, 157:105-32 (1982)), or in Stryer, supra.

"Cytoplasmic domains" refers to the domains of T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "ligand-binding region" refers to sequences derived from a chemosensory or taste receptor that substantially incorporates transmembrane domains II to VII (TM II to VII). The region may be capable of binding a ligand, and more particularly, a taste eliciting compound.

The term "plasma membrane translocation domain" or simply "translocation domain" means a polypeptide domain that is functionally equivalent to an exemplary translocation domain (5'-MNGTEGPNFYVPFSNKTGVV; SEQ ID NO: 7). These peptide domains, when incorporated into the amino terminus of a polypeptide coding sequence, can with great efficiency "chaperone" or "translocate" the hybrid ("fusion") protein to the cell plasma membrane. This particular "translocation domain" was initially derived from the amino terminus of the human rhodopsin receptor polypeptide, a 7-transmembrane receptor. Another translocation domain has been derived from the bovine rhodopsin sequence and is also useful for facilitating translocation. Rhodopsin derived sequences are particularly efficient in translocating 7-transmembrane fusion proteins to the plasma membrane.

"Functional equivalency" means the domain's ability and efficiency in translocating newly translated proteins to the plasma membrane as efficiently as exemplary SEQ ID NO: 7 under similar conditions; relative efficiencies can be measured (in quantitative terms) and compared, as described herein. Domains falling within the scope of the invention can be determined by routine screening for their efficiency in translocating newly synthesized polypeptides to the plasma membrane in a cell (mammalian, *Xenopus*, and the like) with the same efficiency as the twenty amino acid long translocation domain SEQ ID NO: 7.

The phrase "functional effects" in the context of assays for testing Compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R proteins receptors are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G Proteins; kinases (e.g., homologs of rhodopsin kinase and beta adrenergic receptor kinases that are involved in deactivation and desensitization of a receptor); and arrestins, which also deactivate and desensitize receptors. Modulators include genetically modified versions of T2R family members, e.g., with altered activity, as well as naturally occurring and synthetic ligands, antagonists, agonists, small chemical molecules and the like.

Such assays for inhibitors and activators include, e.g., expressing T2R family members in cells or cell membranes, applying putative modulator compounds in the presence or absence of compounds that modulate, e.g., bitter compounds, and then determining the functional effects on taste transduction, as described above. Samples or assays comprising T2R family members that are treated with a potential activator, inhibitor, or modulator are compared to control samples without the inhibitor, activator, or modulator to examine the extent of modulation. Control samples (untreated with modulators) are assigned a relative T2R activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated", when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste eliciting compound-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

The term "library" means a preparation that is a mixture of different nucleic acid or poly-peptide molecules, such as the library of recombinant generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., *Nucleic Acid Res.*, 19:5081 (1991); Ohtsuka et al., *J. Biol. Chem.*, 260:2605-08 (1985); Rossolini et al., *Mol. Cell. Probes*, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, *Proteins*, W.H. Freeman and Company (1984); Schultz and Schimer, *Principles of Protein Structure*, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$), thiazole, retroamide, thioamide, or ester (see, e.g., Spatola, *Chemistry and Biochemistry of Amino Acids, Peptides and Proteins*, Vol. 7, 267-357, Marcell Dekker, *Peptide Backbone Modifications*, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridisation with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics.

Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T2R family member from specific species such as rat, mouse, or human can be selected to obtain only those polyclonal antibodies that are specifically immunoreactive with the T2R polypeptide or an immunogenic portion thereof and not with other proteins, except for orthologs or polymorphic variants and alleles of the T2R polypeptide. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual*, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

Based on the foregoing, the present invention provides assays for identifying compounds that block the specific activation of hT2R4, hT2R44 or hT2R61 by bitter compounds. Particularly the invention provides assays, preferably cell-based assays, for identifying compounds that affect (block) the activation of hT2R4 by quinine or related compounds, hT2R61 by 6-nitrosaccharin, saccharin or related compounds, or hT2R44 by denatonium, 6-nitrosaccharin or related compounds. It is anticipated that compounds which block the activation of these hT2Rs by the above-identified bitter testing compounds will specifically inhibit bitter taste elicited by other bitter compounds that interact with these specific hT2Rs.

Particularly, it was found that quinine, a bitter alkaloid, specifically activates T2R4 in a dose-dependent manner. This was discovered in a cell-based assay that detects changes in intracellular calcium concentration. In brief (as discussed in more detail in the examples), human embryonic kidney cells that stably express large T-cell antigen and G15 protein (HEK-G15) were transiently transfected with an hT2R4 expression plasmid (e.g., by use of $Ca^{2+}$ phosphate or by use of lipid-based systems). Additionally, other HEK-G15 cell lines were transiently transfected with other human T2Rs. Thereafter, a fluorescent-based assay was used to detect changes in calcium concentration in the transiently transfected cells. Using this assay, it was found that the addition of quinine to cells that express hT2R4 elicits a signaling cascade leading to the activation of PLC and a subsequent increase in intracellular calcium concentration resulting in an increase of fluorescence which was detected using a calcium-sensitive fluorescent dye. These changes were monitored e.g., using fluorescence microscopic and appropriately designed software (such as Imaging Workstation, Axon). By contrast, using the same assay, quinine did not specifically activate HEK-G15 cells that were transiently transfected with other hT2Rs. Based thereon, it appears that hT2R4 is the human T2R that is specifically activated by quinine and likely structurally related compounds. Consequently, it is anticipated that compounds which block activation of hT2R4 by quinine will inhibit better taste elicited by hT2R4, particularly that elicited by the bitter alkaloid quinine and related compounds that activate hT2R4. Examples of such assays are disclosed in further detail infra.

Also, the invention particularly involves the discovery that hT2R44 is specifically activated by denatonium and 6-nitrosaccharin and that hT261 is specifically activated by 6-nitrosaccharin. This discovery was made using a GTPγS binding assay depicted schematically in FIG. 4. This assay is a classic assay to monitor GPCR activity (see Wessling-Resnick and Johnson, J. Biol. Chem. 262:12444-12447 (1987)). This assay is based on the fact that in the presence of an appropriate ligand the receptor is able to activate G-protein. Thereupon, activated G-protein exchanges bound GDP to GTP.

Moreover, if a non-hydrizable analog of GTP, GTPγS is used, the nucleotide remains tightly bound to the G-protein and can be separated from unbound nucleotide. Therefore, in this assay, the amount of bound GTPγS reflects the amount of activated G-protein, which in turn is an indicator of the extent of receptor activation. The $GTP\gamma^{35}S$ ("GTPγS") binding assay can be practiced using a variety of G-proteins such as gustducin and transducin. As described in the examples which follow, using this assay with transducin as the G-protein, it was observed that insect cells which expressed either hT2R44 (SEQ ID NO.: 3) or hT2R61 (SEQ ID NO.: 5) displayed increased activity in the presence of added bitter compounds.

Particularly, as disclosed in detail in the experimental examples which follow, hT2R61 is activated in the presence of 6-nitrosaccharin and hT2R44 is activated less efficiently by this compound. Additionally, hT2R44 is specifically activated by denatonium benzoate (with activation attributable to the denatonium constituent as demonstrated by the fact that sodium benzoate at comparable concentration did not activate hT2R44).

By contrast denatonium did not activate other hT2Rs expressed using the same transient cell expression system (Sf9 baculovirus expression system) when evaluated by the same binding assay. Also, it was observed that several denatonium derivatives also activated hT2R44, but to a lesser extent than denatonium. Denatonium benzoate is one of the most bitter compounds known to trigger bitter taste in humans. These results suggest that hT2R44 mediates the bitter taste of denatonium in humans and that compounds which block denatonium activation of hT2R44 should modulate (block) bitter taste associated with the activation of this receptor.

Accordingly, the present invention provides assays, preferably cell-based assays, for identifying compounds that modulate (block) hT2R4 activation by quinine or related compounds as a means of identifying compounds that block bitter taste attributable to hT2R4 activation.

Also, the present invention provides assays, preferably cell-based assays, for identifying compounds that modulate (block) hT2R61 activation by 6-nitrosaccharin or saccharin or related compounds as a means of identifying compounds that block bitter taste in humans elicited by hT2R61 activation.

Also, the invention provides assays, preferably cell-based assays, for identifying compounds that block activation of hT2R44 by denatonium or 6-nitrosaccharin, or related compounds, as a means of identifying compounds that block bitter taste in humans elicited by hT2R44 activation. Preferred assays and expression systems useful in invention are described in detail infra.

Most typically, these assays will utilize a test cell that expresses a DNA encoding an hT2R4, hT2R44 or hT2R61 polypeptide having an amino acid sequence as identified previously. However, it is anticipated that fragments, orthologs, variants or chimeras of these receptor polypeptides which retain the functional properties of hT2R4, hT2R44 or hT2R61 will also be useful in these assays. Examples of such variants include splice variants, single nucleotide polymorphisms, allelic variants, and mutations produced by recombinant or chemical means, or naturally occurring. Means for isolation and expression of T2Rs, which are used in the assays of the present invention and assays which are contemplated for use in the present invention to identify compounds that inhibit activation of hT2R4, hT2R44 or hT2R61, are set forth below.

Isolation and Expression of T2Rs

Isolation and expression of the T2Rs, or fragments or variants thereof, of the invention can be effected by well-established cloning procedures using probes or primers constructed based on the T2R nucleic acids sequences disclosed in the application. Related T2R sequences may also be identified from human or other species genomic databases using the sequences disclosed herein and known computer-based search technologies, e.g., BLAST sequence searching. In a particular embodiment, the pseudogenes disclosed herein can be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, *Cold Spring Harbor Symp. Quant. Biol.* 47:411-18 (1982); Adams, *Am. Chem. Soc.,* 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., *Molecular Cloning: A Laboratory Manual* (2nd ed.), Vols. 1-3, Cold Spring Harbor Laboratory (1989); Ausubel, ed., *Current Protocols in Molecular Biology*, John Wiley & Sons, Inc., New York (1997); Tijssen, ed., *Laboratory Techniques in Biochemistry and Molecular Biology: Hybridization With Nucleic Acid Probes, Part I, Theory and Nucleic Acid Preparation*, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T2R ligand-binding region. The nucleic acids described herein can also be cloned or measured quantitatively using amplification techniques. Amplification methods are also well known in the art, and include, e.g., polymerase chain reaction (PCR) (Innis ed., *PCR Protocols, a Guide to Methods and Applications*, Academic Press, N.Y. (1990); Innis ed., *PCR Strategies*, Academic Press, Inc., N.Y. (1995)); ligase chain reaction (LCR) (Wu, *Genomics,* 4:560 (1989); Landegren, *Science,* 241:1077 (1988); Barringer, *Gene,* 89:117 (1990)); transcription amplification (Kwoh, *PNAS,* 86:1173 (1989)); self-sustained sequence replication (Guatelli, *PNAS,* 87:1874 (1990)); Q Beta replicase amplification (Smith, *J. Clin. Microbiol.,* 35:1477-91 (1997)); automated Q-beta replicase amplification assay (Burg, *Mol. Cell. Probes,* 10:257-71 (1996)); and other RNA polymerase mediated techniques (e.g., NASBA, Cangene, Mississauga, Ontario). See also, Berger, *Methods Enzymol.,* 152:307-16 (1987); Sambrook; Ausubel; U.S. Pat. Nos. 4,683,195 and 4,683,202; Sooknanan, *Biotechnology,* 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp El sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T2R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane T2R.

As domain structures and sequence of many 7-membrane T2R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T2R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T2R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is electronically accessible, and is directly linked from the BlockMaker multiple sequence alignment site for hybrid primer prediction beginning with a set of related protein sequences, as known taste receptor ligand-binding regions (see, e.g., Rose, Nucleic Acids Res., 26:1628-35 (1998); Singh, Biotechniques, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.*, 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.*, 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, *PNAS,* 95:4258-63 (1998)). Exemplary degenerate primers of the invention incorporate the nucleobase analog 5'-Dimethoxytrityl-N-benzoyl-2'-deoxy-Cytidine, 3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T2R polypeptides and polymorphic variants, alleles, and interspecies homologs thereof, by detecting expressed homologs immunologically with antisera or purified antibodies made against a T2R polypeptide, which also recognize and selectively bind to the T2R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T2Rs fused to a translocation sequences may be constructed. Also provided are hybrid T2Rs comprising the translocation motifs and taste eliciting compound-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, *Biochimie,* 80:289-93 (1998)), subtilisin protease recognition motif (see, e.g., Polyak, *Protein Eng.,* 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, *Biochemistry,* 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, *DNA Cell. Biol.,* 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, Nature, 328:731 (1987); Berger supra; Schneider, Protein Expr. Purif., 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, Gene, 190:315-17 (1997); Aubrecht, J. Pharmacol. Exp. Ther., 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T2R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, Protein Sci., 2:55-70 (1993). Other alignment and modeling algorithms are well known in the art (see, e.g., Peitsch, Receptors Channels, 4:161-64 (1996); Kyte & Doolittle, J. Md. Biol., 157:105-32 (1982); Cronet, Protein Eng., 6:59-64 (1993).

The present invention also includes not only the nucleic acid molecules and polypeptides having the specified nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T2R family member. Further, a protein fragment of the invention can optionally be an antigenic fragment that is capable of binding to an antibody raised against a T2R family member.

Also contemplated are chimeric proteins, comprising at least 10, 20, 30, 50, 70, 100, or 150 amino acids, or more, of one of at least one of the T2R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T2R polypeptide of the invention. In another embodiment, one portion of the chimera corresponds to, or is derived from the one or more of the transmembrane regions of a T2R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C-terminal domain, or any combination thereof, can be covalently linked to a heterologous protein. For instance, a T2R transmembrane region can be linked to a heterologous GPCR transmembrane domain, or a heterologous GPCR extracellular domain can be linked to a T2R transmembrane region. Other heterologous proteins of choice can include, e.g., green fluorescent protein, β-gal, glutamate receptor, and the rhodopsin N-terminus.

Also within the scope of the invention are host cells for expressing the T2Rs, fragments, or variants of the invention. To obtain high levels of expression of a cloned gene or nucleic acid, such as cDNAs encoding the T2Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., However, bacterial or eukaryotic expression systems can be used.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T2R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Assays for Detection of Compounds that Modulate the Activity of hT2R4, hT2R44 or hT2R61

Methods and compositions for determining whether a test compound specifically binds to a T2R polypeptide of the invention, both in vitro and in vivo are described below. Many aspects of cell physiology can be monitored to assess the effect of ligand-binding to a naturally occurring or chimeric T2Rs. These assays may be performed on intact cells expressing a T2R polypeptide, on permeabilized cells, or on membrane fractions produced by standard methods.

Taste receptors bind taste eliciting compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The T2R proteins or polypeptides of the assay will typically be selected from a polypeptide having a sequence contained in SEQ ID NOS.: 1, 3 or 5, or fragments or conservatively modified variants thereof.

Alternatively, the T2R proteins or polypeptides of the assay can be derived from a eukaryotic host cell, and can include an amino acid sequence having amino acid sequence identity to SEQ ID NOS.: 1, 3 or 5, or conservatively modified variants thereof. Generally, the amino acid sequence identity will be at least 30% preferably 30-40%, more specifically 50-60, 70%, 75%, 80%, 85%, 90%, 95%, 96%, 97%, 98%, or 99%. Optionally, the T2R proteins or polypeptides of the assays can comprise a region of a T2R polypeptide, such as an extracellular domain, transmembrane region, cytoplasmic domain, ligand-binding domain, and the like. Optionally, the T2R polypeptide, or a portion thereof, can be covalently linked to a heterologous protein to create a chimeric protein used in the assays described herein.

Modulators of T2R activity may be tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

Detection of Modulators

Compositions and methods for determining whether a test compound specifically binds to a T2R receptor of the invention, both in vitro and in vivo, are described below. Many aspects of cell physiology can be monitored to assess the effect of ligand binding to a T2R polypeptide of the invention. These assays may be performed on intact cells expressing a chemosensory receptor, on permeabilized cells, or on membrane fractions produced by standard methods or in vitro using de novo synthesized proteins.

In vivo, taste receptors bind to taste modulatory compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Alternatively, the T2R proteins or polypeptides of the assay can be derived from a eukaryotic host cell and can include an amino acid subsequence having amino acid sequence identity to the T2R polypeptides disclosed herein, or fragments or conservatively modified variants thereof. Generally, the amino acid sequence identity will be at least 35 to 50%, or optionally 75%, 85%, 90%, 95%, 96%, 97%, 98%, or 99%. Optionally, the T2R proteins or polypeptides of the assays can comprise a domain of a T2R protein, such as an extracellular domain, transmembrane region, transmembrane domain, cytoplasmic domain, ligand-binding domain, and the like. Further, as described above, the T2R protein or a domain thereof can be covalently linked to a heterologous protein to create a chimeric protein used in the assays described herein.

Modulators of T2R receptor activity are tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

1. In Vitro Binding Assays

Taste transduction can also be examined in vitro with soluble or solid state reactions, using the T2R polypeptides of the invention. In a particular embodiment, T2R ligand-binding domains can be used in vitro in soluble or solid state reactions to assay for ligand binding.

It is possible that the ligand-binding domain may be formed by the N-terminal domain together with additional portions of the extracellular domain, such as the extracellular loops of the transmembrane domain.

In vitro binding assays have been used with other GPCRs, such as the metabotropic glutamate receptors (see, e.g., Han and Hampson, *J. Biol. Chem.* 274:10008-10013 (1999)). These assays might involve displacing a radioactively or fluorescently labeled ligand, measuring changes in intrinsic fluorescence or changes in proteolytic susceptibility, etc.

Ligand binding to a T2R polypeptide according to the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbence, refractive index) hydrodynamic (e.g., shape), chromatographic, or solubility properties.

In a preferred embodiment of the invention, a [$^{35}$S]GTPγS binding assay is used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled [$^{35}$S]GTPγS to the G protein in the presence of a putative ligand. Typically, membranes containing the chemosensory receptor of interest are mixed with a G protein. Potential inhibitors and/or activators and [$^{35}$S]GTPγS are added to the assay, and binding of [$^{35}$S]GTPγS to the G protein is measured. Binding can be measured by liquid scintillation counting or by any other means known in the art, including scintillation proximity assays (SPA). In other assays formats, fluorescently labeled GTPγS can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T2R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor taste eliciting compound-binding which may activate or inhibit the chemosensory receptors of the invention, fluorescence-labeled taste eliciting compounds or auto-fluorescent taste eliciting compounds may be used.

Fluorescence polarization (P) is defined as:

$$P = \frac{Int_{\|} - Int_{\perp}}{Int_{\|} + Int_{\perp}}$$

Where II is the intensity of the emission light parallel to the excitation light plane and Int ⊥ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240, which gives a thorough explanation of this equation. Summarily, the Perrin equation states that polarization is directly proportional to the rotational relaxation time, the time that it takes a molecule to rotate through an angle of approximately 68.5° Rotational relaxation time is related to viscosity (η), absolute temperature (T), molecular volume (V), and the gas constant (R) by the following equation:

$$\text{Rotational Relaxation Time} = \frac{3\eta V}{RT}$$

The rotational relaxation time is small (≈1 nanosecond) for small molecules (e.g. fluorescein) and large (≈100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

A. Solid State and Soluble High Throughput Assays

In yet another embodiment, the invention provides soluble assays using a T2R polypeptide; or a cell or tissue expressing a T2R polypeptide. In another embodiment, the invention provides solid phase based in vitro assays in a high throughput format, where the T2R polypeptide, or cell or tissue expressing the T2R polypeptide is attached to a solid phase substrate or a taste stimulating compound and contacted with a T2R receptor, and binding detected using an appropriate tag or antibody raised against the T2R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.,* 85:2149-2154 (1963) (describing solid phase synthesis of, e.g., peptides); Geysen et al., *J. Immun. Meth.,* 102:259-274 (1987) (describing synthesis of solid phase components on pins); Frank & Doring, *Tetrahedron,* 44:60316040 (1988) (describing synthesis of various peptide sequences on cellulose disks); Fodor et al., *Science,* 251:767-777 (1991); Sheldon et al., *Clinical Chemistry,* 39(4):718-719 (1993); and Kozal et al., *Nature Medicine,* 2(7):753759 (1996) (all describing arrays of biopolymers fixed to solid substrates). Non-chemical approaches for fixing tag binders to substrates include other common methods, such as heat, cross-linking by UV radiation, and the like.

3. Cell-Based Assays

In one preferred embodiment, a T2R protein is expressed in a eukaryotic cell either in unmodified forms or as chimeric, variant or truncated receptors with or preferably without a heterologous, chaperone sequence that facilitates its maturation and targeting through the secretory pathway. Such T2R polypeptides can be expressed in any eukaryotic cell, such as HEK-293 cells. Preferably, the cells comprise a functional G protein, e.g., $G\alpha15$, that is capable of coupling the chimeric receptor to an intracellular signaling pathway or to a signaling protein such as phospholipase C. Activation of T2R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., *Methods in Enzymology,* vols. 237 and 238 (1994) and volume 96 (1983); Bourne et al., *Nature,* 10:349:117-27 (1991); Bourne et al., *Nature,* 348:125-32 (1990); Pitcher et al., *Annu. Rev. Biochem.,* 67:653-92 (1998).

T2R modulation may be assayed by comparing the response of T2R polypeptides treated with a putative T2R modulator to the response of an untreated control sample or a sample containing a known "positive" control. Such putative T2R modulators can include molecules that either inhibit or activate T2R polypeptide activity. In one embodiment, control samples treated with a compound that activates the T2R are assigned a relative T2R activity value of 100. Inhibition of a T2R polypeptide is achieved when the T2R activity value relative to the control sample is about 90%, optionally 50%, optionally 25-0%. Activation of a T2R polypeptide is achieved when the T2R activity value relative to the control is 110%, optionally 150%, 200-500%, or 1000-2000%.

Changes in ion flux may be assessed by determining changes in ionic polarization (i.e., electrical potential) of the cell or membrane expressing a T2R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., *New Engl. J. Med.,* 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., *J. Membrane Biol.,* 88:67-75 (1988); Gonzales & Tsien, *Chem. Biol.,* 4:269-277 (1997); Daniel et al., *J. Pharmacol. Meth.,* 25:185-193 (1991); Holevinsky et al., *J. Membrane Biology,* 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as $G\alpha15$ and $G\alpha16$ can be used in the assay of choice (Wilkie et al., *Proc. Nat'l Acad. Sci.,* 88:10049-10053 (1991)).

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T2R polypeptide activity is measured by expressing T2R gene in a heterologous cell with a promiscuous G protein that links the receptor to a phospholipase C signal transduction pathway (see Offermanns & Simon, J. Biol. Chem., 270:15175-15180 (1995)). Optionally the cell line is HEK-293 (which does not normally express T2R genes) and the promiscuous G protein is Gα15 (Offermanns & Simon, supra). Modulation of taste transduction is assayed by measuring changes in intracellular $Ca^{2+}$ levels, which change in response to modulation of the T2R signal transduction pathway via administration of a molecule that associates with the T2R polypeptide. Changes in $Ca^{2+}$ levels are optionally measured using fluorescent $Ca^{2+}$ indicator dyes and fluorometric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, J. Bio. Chem., 270:15175-15180 (1995), may be used to determine the level of cAMP. Also, the method described in Felley-Bosco et al., Am. J. Resp. Cell and Mol. Biol., 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T2R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, beta-galactosidase beta-lactamase and alkaline phosphatase. Furthermore, the protein of interest can be used as an indirect reporter via attachment to a second reporter such as green fluorescent protein (see, e.g., Mistili & Spector, Nature Biotechnology, 15:961-964 (1997)).

The amount of transcription is then compared to the amount of transcription in either the same cell in the absence of the test compound, or it may be compared with the amount of transcription in a substantially identical cell that lacks the T2R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T2R polypeptide of interest.

4. Transgenic Non-Human Animals Expressing Chemosensory Receptors

Non-human animals expressing one or more taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T2R sequences of the invention can be for example expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, Transgenic Res 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol. Genet.* 7:53-62 (1998); Moreadith, *J. Mol. Med.* 75:208-216 (1997); Tojo, *Cytotechnology* 19:161-165 (1995); Mudgett, *Methods Mol. Biol.* 48:167-184 (1995); Longo, *Transgenic Res.* 6:321-328 (1997); U.S. Pat. Nos. 5,616,491; 5,464,764; 5,631,153; 5,487,992; 5,627,059; 5,272,071; WO 91/09955; WO93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T2R gene sequences can replace the orthologs T2R in the mouse genome. In this way, a mouse expressing a human or rat T2R is produced. This mouse can then be used to analyze the function of human or rat T2Rs, and to identify ligands for such T2Rs.

Modulators

The compounds tested as modulators of a T2R family member can be any small chemical compound, or a biological entity, such as a protein, sugar, nucleic acid or lipid. Alternatively, modulators can be genetically altered versions of a T2R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-93 (1991) and Houghton et al., *Nature*, 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al., *PNAS.*, 90:6909-13 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-18 (1992)), analogous organic syntheses of small compound libraries (Chen et al., *J. Amer. Chem. Soc.*, 116:2661 (1994)), oligocarbamates (Cho et al., *Science*, 261:1303 (1993)), peptidyl phosphonates (Campbell et al., *J. Org. Chem.*, 59:658 (1994)), nucleic acid libraries (Ausubel, Berger, and Sambrook, all supra), peptide nucleic acid libraries (U.S. Pat. No. 5,539,083), antibody libraries (Vaughn et al., *Nature Biotechnology*, 14(3):309-14 (1996) and PCT/US96/10287), carbohydrate libraries (Liang et al., *Science*, 274:1520-22 (1996) and U.S. Pat. No. 5,593, 853), small organic molecule libraries (benzodiazepines, Baum, C&EN, Jan. 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T2R modulators can be used in any food product, confectionery, pharmaceutical composition, or ingredient thereof to thereby modulate the taste of the product, composition, or ingredient in a desired manner. For instance, T2R modulators that enhance bitter taste sensation can be added to provide a bitter taste to a product or composition, while T2R modulators which block bitter taste sensations can be added to improve the taste of a product or composition.

Use of Compounds Identified by the Invention

Compounds identified according to the invention may be added to foods, beverages or medicinal compositions to modulate, preferably block bitter taste triggered by activation of hT2R4, hT2R44 or hT2R61 by tasting testing compounds. Particularly, compounds that block activation of hT2R4 by quinine or related compounds may be used as additives in foods, beverages or esmedicinals that would otherwise elicit a bitter taste. For example, these compounds may be added to medicinals preparations that contain quinine or related bitter compounds in an amount effective to inhibit bitter taste.

Compounds that block 6-nitrosaccharin or saccharin activation of hT2R44 or hT2R61 can be used in foods, beverages or medicinals products to block the bitter taste of saccharin or other bitter compounds that activate hT2R61 or T2R44. Particularly, it is anticipated that compounds identified using the disclosed assays may be included in saccharin containing diet beverages to inhibit bitter taste associated therewith.

Finally, compounds which inhibit denatonium activation of hT2R44 are useful as additives in foods, beverages or medicinal preparations to block bitter taste attributable to activation of the hT2R44 receptor. As denatonium is a highly potent bitter compound, compounds that inhibit the hT2R44 receptor should effectively inhibit the bitter taste of a variety of bitter compounds. This is evidenced by the fact that this receptor is activated by several denatonium derivatives.

Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis.

The following articles provide an overview of the art of in situ hybridization: Singer et al., *Biotechniques*, 4:230250 (1986); Haase et al., *Methods in Virology*, vol. VII, 189-226 (1984); and Names et al., eds., *Nucleic Acid Hybridization: A Practical Approach* (1987). In addition, a T2R protein can be detected with the various immunoassay techniques described above. The test sample is typically compared to both a positive control (e.g., a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a functional T2R polypeptide. A wide variety of kits and components can be prepared according to the present invention, depending upon the intended user of the kit and the particular needs of the user.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Example 1

In this example, we show that quinine, a bitter alkaloid, specifically activates hT2R4, a human bitter receptor having the DNA sequence contained in SEQ ID NO: 2 in this application.

Activation of hT2R4 by quinine is measured in a cell-based assay detecting changes in intracellular calcium concentration. In brief, human embryonic kidney cells stably expressing the large T-cell antigen and the promiscuous G protein G15 (HEK-G15) are transiently transfected with the hT2R4 plasmid either by $Ca^{2+}$ phosphate or lipid-based systems. Transiently transfected cells are seeded into 24 well culture plates, and functional expression allowed to proceed for a total of 48 hours. The cells are then incubated with a fluorescent dye specific for calcium (Fluo-4 or Fura-2; Molecular Probes) that provides a fast, simple and reliable fluorescence-based method for detecting changes in calcium concentration inside the cell. Addition of quinine to cells elicits a signaling cascade leading to the activation of PLC and a subsequent increase in intracellular calcium concentration. This increase in calcium concentration changes the fluorescence properties of the calcium dye inside the cells. These changes are monitored using fluorescence microscopy and a specific design software (Imaging Workbench, Axon). Using this approach we observed that quinine specifically activates cells (increases intracellular calcium concentration) expressing hT2R4. The parental line (HEK-G15) or HEK-G15 transiently transfected with other hT2Rs do not exhibit comparable responses to quinine (see FIG. 1).

Example 2

A HEK-G15 line stably expressing high levels of hT2R4 on its cell surface (HEK-G15-hT2R4) is also used in high throughput screening assays to find potent hT2R4 antagonists. We generated a stable HEK-G15-hT2R4 line that expresses 2-3 times more receptors at the cell surface than transiently transfected cells (see FIG. 2). In this platform, the cells are seeded into 96 well or 384 well culture plates 18-24 hours before the assay. The cells are then incubated with the fluorescent calcium sensitive dye (Molecular Devices) and are stimulated and read in a standard fluorescence intensity plate reader (FLIPR or VIPR). Using this approach we have been able to further characterize the quinine effect on hT2R4. We found that quinine activates hT2R4 in a typical dose-response relationship (see FIG. 3).

Example 3

In this experiment, to monitor activation of T2R receptors we employed a GTPγS binding assay (FIG. 4). This assay is a classic assay to monitor the activity of GPCRs (Wessling-Resnick and Johnson, 1987). It is based on the fact that in the presence of an appropriate ligand, a GPCR is able to activate G protein. The resultant activated G protein exchanges bound GDP to GTP. If a nonhydrolysable analog of GTP, GTPγS is used the nucleotide remains tightly bound to G protein and can be separated from unbound nucleotide. The use of radioactively labeled [γ-$^{35}$S]GTPγS allows determination of the amount of bound GTPγS. The amount of bound GTPγS reflects the amount of activated G protein, which in turns reflects activation of the receptor. We used transducin as a G protein in GTPγS binding assay. Transducin is expressed in the visual system and is an ortholog of gustducin. Transducin was purified from bovine retinas (Stryer, Methods Enzymol 96:617-627 (1983)).

The assay reactions contained 15-20 μg of total protein from Sf9 cell membranes expressing appropriate hT2Rs, 0.2 μM transducin in 30 μl of buffer B (30 mM Tris-HCl, pH 8, 100 mM NaCl, 3 mM MgCl$_2$, 1 mM DTT). Some reactions also included 0.05-10 mM of tested bitter compounds. Reactions were initiated by the addition of 0.3 μM [γ-$^{35}$S]GTPγS (50 Ci/mmol), carried on at 30° C. for 1 hour, stopped by the addition of 170 μl of 0.5 mM GTP in buffer B and then filtered through nitrocellulose filters. The amount of bound [$^{35}$S]GTPγS was determined by liquid scintillation counter.

All 24 known hT2Rs and mT2R5 were expressed in Sf9 cells using a baculovirus expression system. These T2R constructs had N-terminal tag consisting of 40 N-terminal rhodopsin amino acids added to coding sequences. Sf9 cells were infected with appropriate baculoviruses at a ratio of 10-20 microliters of amplified viral stock per $10^6$ of cells. Cells were harvested and processed for analysis 2 days post-infection. Expression of all tested T2Rs was confirmed by immunoblotting using anti-rhodopsin tag antibodies (B6-30). Membrane preparations were generated essentially as described by treating Sf9 membranes with 5M urea (Ryba, J. Biol. Chem. 270(12): 6757-6767 (1995)). Membranes were then washed with buffer (20 mM Tris-HCl, pH 8, 0.5 mM EDTA, 1 mM DTT) and resuspended to a final concentration ~2.5-3 mg of total protein/ml.

All hT2Rs were tested with a set of 10 bitter compounds in GTPγS binding assay with transducin. Two hT2Rs, hT2R44 and hT2R61 displayed increased activity in the presence of added bitter compounds.

Particularly, it was shown that hT2R61 activity is increased in the presence of 6-nitrosaccharin. Of all tested hT2Rs only one other receptor (hT2R44, see below) was activated in the presence of 6-nitrosaccharin yet less efficiently, whereas even the most closely related hT2R, –hT2R64 (89% amino acid sequence identity to hT2R61), was not activated (FIG. 5). 6-nitrosaccharin is a bitter analog of saccharin. It activates hT2R61 at concentrations (0.1-0.5 mM, FIG. 5) that humans also perceive as bitter. At these concentrations saccharin does not significantly activate hT2R61, and most humans do not taste it as bitter. The correlation between biochemical and human psychophysical data indicate that hT2R61 is a human receptor for bitter taste of 6-nitrosaccharin.

Many people find that at higher concentrations (2-10 mM) saccharin itself, which is a potent sweetener, has an unpleasant taste that is described as "bitter" or "metallic". Although at low concentrations saccharin does not significantly activate hT2R61, the structural similarity between saccharin and 6-nitrosaccharin suggests that at higher concentrations of saccharin its bitter taste in humans might also be mediated by hT2R61.

It was also observed that hT2R44 activity is increased in the presence of denatonium benzoate. No other tested hT2Rs displayed elevated activity in the presence of this compound. Activation of hT2R44 by denatonium was found to be concentration dependent (FIG. 6). At concentrations of denatonium above 0.3 mM the amount of bound GTPγS is decreased due to nonspecific inhibitory effect denatonium has in the assay. The active ingredient of denatonium benzoate is denatonium, not benzoate, because in the presence of 100 μM sodium benzoate the activity of hT2R44 is unchanged. 6-nitrosaccharin also activates hT2R44, although significantly less.

Denatonium benzoate (benzyldiethyl[(2,6-xylylcarbomoyl)methyl]ammonium benzoate) is one of the most potent bitter compounds known to humans, and it is used widely to study bitter taste. In one such study A. Saroli (Saroli, (Id.) (1984); Saroli, (Id.) (1985)) looked at the relationship between structure of denatonium derivatives and their bitter taste in humans. This study demonstrated that selective changes in the denatonium molecule result in the specific reduction of the compound bitterness, which is reflected in the increased bitter thresholds for humans. To confirm that hT2R44 may mediate bitter taste of denatonium and its derivatives in humans we synthesized three denatonium derivative compounds described by A. Saroli (Id) (1984) and (1985) [(carboxymethyl)methyl]ammonium chloride (DD#2), benzyldimethyl[(2,6-xylylcarbamoyl)methyl]ammonium chloride (DD#3) and benzylmethylethyl[(2,6-xylylcarbamoyl)methyl]ammonium chloride (DD#4) were synthesized. These compounds were tested for their ability to activate hT2R44 and compared to that of denatonium.

As shown in FIG. 7, denatonium derivatives have weaker abilities to activate hT2R44 compared to denatonium. There is a very good correlation between a compounds' ability to activate hT2R44 and its relative bitterness in human taste studies. These results argue compellingly that hT2R44 mediates bitter taste of denatonium and its derivatives in humans. It was previously suggested that denatonium activates hT2R4 (Chandrashekar et al., (Id) (2000)). However, effective denatonium concentration used in that study (1.5 mM) was unusually high. It is $10^5$-fold higher than the reported bitter threshold for denatonium to humans (Saroli, (Id.) (1984)). Thus, it is likely that denatonium has a nonspecific effect on hT2R4. We showed that hT2R44 is also activated by 6-nitrosaccharin, however, it displays significantly lower activity in the presence of 6-nitrosaccharin than hT2R61. Thus, it is likely that hT2R61 is a primary mediator of bitter taste of 6-nitrosaccharin, whereas hT2R44 mediates bitter taste of 6-nitrosaccharin at higher concentrations.

While the foregoing detailed description has described several embodiments of the present invention, it is to be understood that the above description is illustrative only and not limiting of the disclosed invention. The invention is to be limited only by the claims which follow.

---

What is claimed is:

1. An in vitro assay method for identifying a compound which particularly modulates hT2R44 receptor associated bitter taste comprising: (i) screening a compound for its effect on the activation of a bitter taste receptor polypeptide that is at least 90% identical to the hT2R44 polypeptide of SEQ ID NO:3 by saccharin or 6-nitrosaccharin; and (ii) determining whether said compound modulates hT2R44 associated bitter taste based on its ability to modulate the activation of said receptor by saccharin or 6-nitrosaccharin.

2. The assay of claim 1 wherein said bitter taste receptor polypeptide has the amino acid sequence contained in SEQ ID NO.: 3.

3. The assay of claim 1 wherein said bitter taste receptor polypeptide is expressed on a cell membrane.

4. The assay of claim 3 wherein said cell membrane is isolated.

5. The assay of claim 3 wherein said cell membrane is on an intact cell.

6. The assay of claim 5 wherein said cell is a eukaryotic cell.

7. The assay of claim 5 wherein said cell is a mammalian cell or insect cell.

8. The assay of claim 7 wherein said mammalian cell is selected from an HEK cell, BHK cell, COS cell and CHO cell.

9. The assay of claim 1 wherein the modulatory effect of said compound is further confirmed by a taste test.

10. The method of claim 1 wherein said effect on said compound is selected based on changes in intracellular ion concentration.

11. The method of claim 10 wherein said ion is calcium.

12. The method of claim 10 wherein said ion is sodium.

13. The method of claim 1 wherein said compound is selected based on its effect on cell membrane potential.

14. The method of claim 1 wherein said compound is selected based on its ability to block interaction of said receptor polypeptide with saccharin or 6-nitrosaccharin.

15. The method of claim 5 wherein a DNA encoding said bitter taste receptor polypeptide is operably linked to a sequence that facilitates plasma membrane export.

16. The method of claim 5 wherein said cell line is an HEK-293 cell line.

17. The method of claim 1 wherein the effect of said compound on said bitter taste receptor polypeptide is assayed based on change in intracellular cAMP, cGMP or IP3.

18. The method of claim 11 wherein the difference in calcium ion concentration is monitored using a reporter molecule.

19. The method of claim 18 wherein said reporter molecule is a fluorescent dye specific for calcium.

* * * * *